United States Patent
Vicari et al.

(10) Patent No.: US 9,580,312 B2
(45) Date of Patent: Feb. 28, 2017

(54) METHOD FOR PRODUCING ACETYLENES AND SYNGAS

(71) Applicant: BASF SE, Ludwigshafen (DE)

(72) Inventors: Maximilian Vicari, Limburgerhof (DE); Christian Weichert, Bad Duerkheim (DE); Dirk Grossschmidt, Mannheim (DE); Michael Russ, Roemerberg (DE); Kai Rainer Ehrhardt, Speyer (DE); Horst Neuhauser, Dudenhofen (DE); Michael L. Hayes, Gonzales, LA (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/758,649

(22) PCT Filed: Jan. 15, 2014

(86) PCT No.: PCT/EP2014/050652
§ 371 (c)(1),
(2) Date: Jun. 30, 2015

(87) PCT Pub. No.: WO2014/111396
PCT Pub. Date: Jul. 24, 2014

(65) Prior Publication Data
US 2015/0336858 A1 Nov. 26, 2015

Related U.S. Application Data

(60) Provisional application No. 61/753,019, filed on Jan. 16, 2013.

(51) Int. Cl.
*C01B 3/38* (2006.01)
*C01B 3/36* (2006.01)
*C07C 2/78* (2006.01)

(52) U.S. Cl.
CPC ............... *C01B 3/36* (2013.01); *C07C 2/78* (2013.01); *C01B 2203/025* (2013.01);
(Continued)

(58) Field of Classification Search
CPC .................................... C07C 2/78; C01B 3/36
See application file for complete search history.

(56) References Cited

U.S. PATENT DOCUMENTS 3,531,265 A * 9/1970 Dille .................... C01B 3/36
  210/722
3,725,270 A * 4/1973 Tassoney ............... C01B 3/36
  210/750

(Continued)

FOREIGN PATENT DOCUMENTS

EP        1 989 160       11/2008
WO    WO 2007/096271 A1    8/2007
(Continued)

OTHER PUBLICATIONS

International Search Report and Written Opinion issued Apr. 4, 2014 in PCT/EP2014/050652.
Ullmann's Encyclopedia of Industrial Chemistry, vol. A1, 1984, pp. 97-145 (with Cover Page).
Peter Passler, et al., "Acetylene" Ullmann's Encyclopedia of Industrial Chemistry, XP002722234, Oct. 15, 2011, pp. 284-293 (with Intro page).

*Primary Examiner* — Melvin C Mayes
*Assistant Examiner* — Kenneth Vaden
(74) *Attorney, Agent, or Firm* — Oblon, McClelland, Maier & Neustadt, L.L.P.

(57) ABSTRACT

The invention relates to a continuous method for producing acetylenes and syngas by partially oxidizing hydrocarbons with oxygen. A first feed stream (1) containing one or more hydrocarbons and a second feed stream (2) containing oxygen are —mixed in a ratio of the mass flows of the second feed stream (2) to the first feed stream (1) corresponding to an oxygen number of less than or equal to 0.31, said streams being heated separately from each other, —and fed to a combustion chamber (FR) via a burner block (BR), the partial oxidation of the hydrocarbons being carried out in said combustion chamber, —thereby obtaining a first cracked gas stream $I_g$. The invention is characterized in that —the first cracked gas stream $I_g$ is precooled to a temperature ranging from 100 to 1000° C. in a prequench region (H), thereby obtaining a second cracked gas stream $II_g$, —50 to 90% of the solids contained in the second cracked gas stream $II_g$ are separated therefrom in a solid-gas separating device (A), thereby obtaining a solid stream $I_f$ and a third cracked gas stream $III_g$, —the third cracked gas stream $III_g$ is cooled to 80 to 90° C. by injecting water in a total quench region (Continued)

(B), thereby obtaining a fourth cracked gas stream $IV_g$ and a first process water stream $I_{liq}$, —the fourth cracked gas stream $IV_g$ undergoes a fine separation of solids in one or more scrubbing devices (C, D), thereby obtaining one or more process water streams $II_{liq}$, $III_{liq}$ and a product gas stream $VI_g$, —the process water streams $I_{liq}$, $II_{liq}$, $III_{liq}$ are merged into a combined process water stream $IV_{liq}$, —the combined process water stream $IV_{liq}$ is partly recirculated, as stream $V_{liq}$, into the total quench region (B) and otherwise undergoes a cleaning process, as stream $VI_{liq}$, by means of a partial evaporation process, thereby obtaining a cleaned process water stream $VII_{liq}$, —which is cooled by a recooling device (F), partially recycled, as stream $VIII_{liq}$, into the method, and otherwise discharged, as stream $IX_{liq}$.

13 Claims, 1 Drawing Sheet

(52) U.S. Cl.
CPC ...... *C01B 2203/0255* (2013.01); *C01B 2203/062* (2013.01); *C01B 2203/0877* (2013.01); *C01B 2203/0894* (2013.01); *C01B 2203/1235* (2013.01); *C01B 2203/148* (2013.01)

(56) References Cited

U.S. PATENT DOCUMENTS

| | | | | |
|---|---|---|---|---|
| 3,820,964 | A | * | 6/1974 | Janka .......................... C10J 3/08 48/111 |
| 3,843,744 | A | * | 10/1974 | Kramer ................... C01B 3/363 208/48 R |
| 5,824,834 | A | * | 10/1998 | Bachtler ................... C01B 3/36 585/537 |
| 8,680,340 | B2 | | 3/2014 | Seeber et al. |
| 2009/0023970 | A1 | | 1/2009 | Bachtles et al. |
| 2012/0119150 | A1 | | 5/2012 | Grobschmidt et al. |
| 2013/0334464 | A1 | | 12/2013 | Vicari et al. |
| 2015/0217999 | A1 | | 8/2015 | Vicari et al. |

FOREIGN PATENT DOCUMENTS

| | | | | |
|---|---|---|---|---|
| WO | WO 2007096271 A1 | * | 8/2007 | ................ C07C 2/78 |
| WO | WO 2012/062584 A1 | | 5/2012 | |
| WO | WO 2012/062784 A1 | | 5/2012 | |
| WO | WO 2012062784 A1 | * | 5/2012 | .............. B01J 4/004 |

* cited by examiner

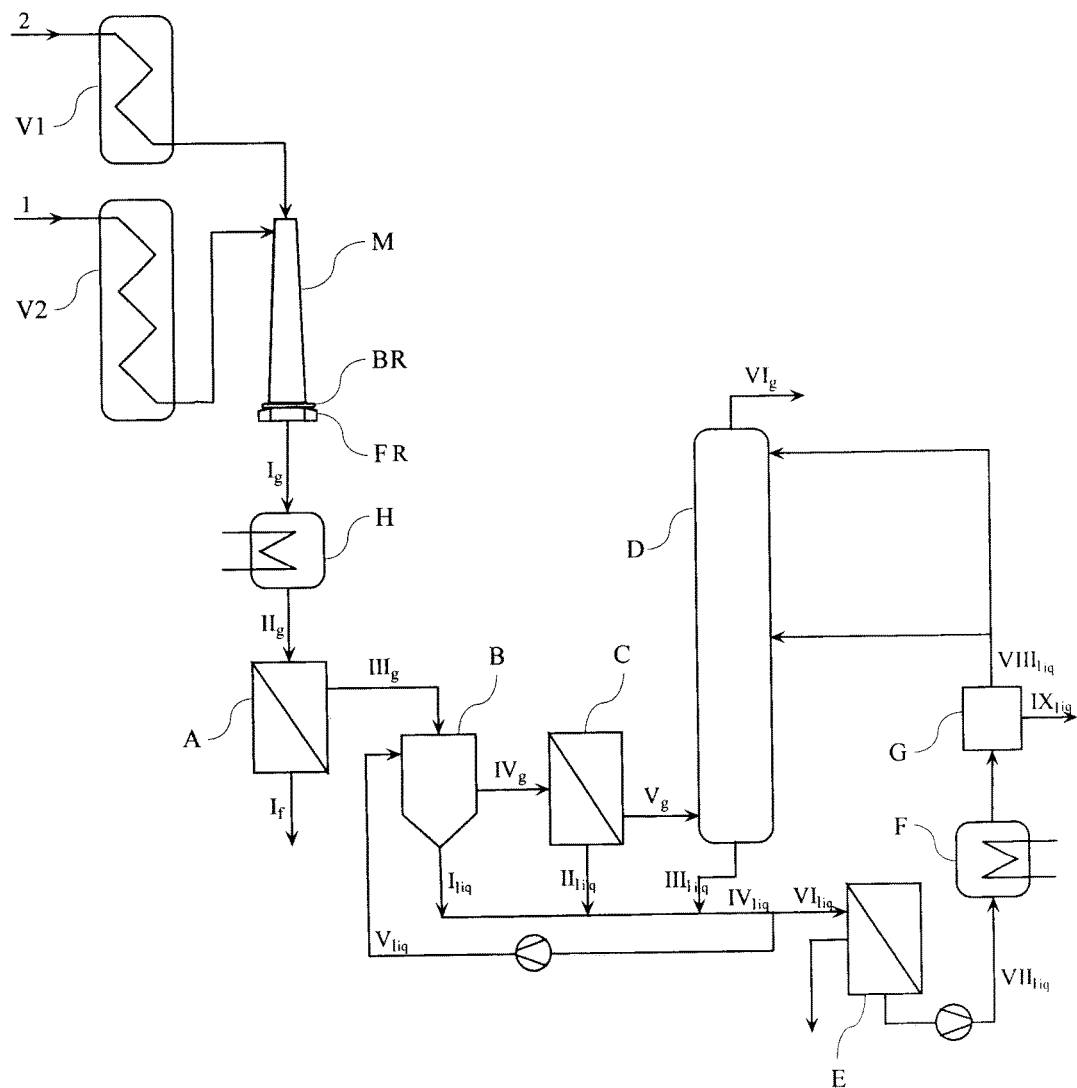

METHOD FOR PRODUCING ACETYLENES AND SYNGAS

The present invention relates to a process for preparing acetylene and synthesis gas by partial oxidation of hydrocarbons with oxygen.

The above partial oxidation is a high-temperature reaction which is typically conducted in a reactor system comprising a mixing unit, a burner block and a quench unit, and is described, for example, in Ullmanns Encyclopedia of Industrial Chemistry (5$^{th}$ Edition, Volume A1, pages 97-144).

According to Ullmanns Encyclopedia of Industrial Chemistry (5$^{th}$ Edition, Volume A1, pages 97-144), the feedstocks are heated separately in preheaters. The heated feedstocks are mixed in a mixing unit and supplied via a mixing diffuser to a burner and further to a combustion chamber. Downstream of the combustion chamber, nozzles are used to supply an aqueous quench medium to the cracking gas, which is cooled rapidly to about 80-90° C. Through suitable selection of the oxygen ratio $\lambda$ ($\lambda$<0.31), the process is conducted such that the yield of acetylene based on the dry cracking gas is at an optimum (>8%). In this context, oxygen ratio $\lambda$ is understood to mean the ratio of the amount of oxygen actually present to the stoichiometrically necessary amount of oxygen required for the full combustion of the feedstocks. At the same time, the soot loading of the cracking gas is also at a maximum. The soot formed from the gas phase in the combustion chamber is partly precipitated by the quench, in a downstream cooling column and a downstream electrostatic filter. The product gas stream containing products of value is removed separately via the cooling column. Downstream of the electrostatic filter, the soot concentration in the remaining cracking gas (without products of value) has fallen to about 1 mg/m$^3$. The soot present in the process water from the quench, the cooling column and the electrostatic filter has a high hydrocarbon content and is therefore hydrophobic, which causes it to float on the process water. Therefore, this soot-laden process water is passed through what are called open soot channels with surface particulate precipitators. The floating soot components are removed and sent to firing. The process water cleaned therein is subsequently run through an open cooling tower and thus cooled. In the course of this, and during the solid-liquid separation beforehand, a majority of the hydrocarbons bound in liquid and gaseous form in the process water, especially aromatics, alkynes, benzene-toluene-xylene, etc., is emitted into the ambient air together with portions of the process water. Subsequently, the loss of process water which has thus arisen is compensated for by addition and the water circuit is closed in the direction of cooling column and quench.

The emissions of hydrocarbons from the process water from the cooling tower (i.e. in an open process water mode), however, are no longer acceptable under the applicable environmental protection regulations. Nor is a closed process water mode an acceptable solution, since the hydrocarbons would accumulate here and lead to polymerization and blockage of the plant.

A further emission source is that of the open soot channels. The solids deposited in the soot channels from the process water have to be dried in a complex manner prior to possible commercial marketing, which makes them unattractive.

A further process for preparing acetylene and synthesis gas by partial oxidation of hydrocarbons with oxygen is described in U.S. Pat. No. 5,824,834. This is a closed water quench process which is optimized for soot volumes and is operated with a lean feed stream, specifically with a feed stream having an oxygen ratio $\lambda$>0.31. However, the process has the disadvantage of a reduced yield of acetylene product of value.

In this process variant, the aqueous quench medium is likewise supplied by means of nozzles to the cracking gas which is cooled rapidly to about 80-90° C. The soot formed from the gas phase in the combustion chamber is partly precipitated by the quench, a downstream cooling column operated with recirculating water, and a downstream electrostatic filter. The product gas stream containing products of value is removed separately via the cooling column. The process is operated here through selection of the oxygen ratio $\lambda$ ($\lambda$>0.31) such that the soot volume obtained in the cracking gas is so low that solely the discharge of the water of reaction obtained from the incineration can ensure steady-state operation. This, however, reduces the acetylene content in the dry cracking gas by 2 percentage points compared to the above-described process, to about 6% by volume. This enables a closed water quench mode, i.e. one isolated from the environment. The advantage over the above-described process variant is thus the possibility of closed operation without further separation apparatus. The disadvantage is yield losses based on the acetylene product of value and target product. In addition, it is likewise the case that the solids separated out of the process water have to be dried in a complex manner prior to possible commercial marketing, which makes them unattractive.

A third process for preparing acetylene and synthesis gas by partial oxidation of hydrocarbons with oxygen is described in EP-A 12171956. This is a process which combines the advantages of the two above-described processes, i.e. optimized yield of acetylene product of value according to Ullmanns Encyclopedia of Industrial Chemistry, 5th Edition, Volume A1, pages 97-144 and compliance with applicable environmental protection regulations in accordance with U.S. Pat. No. 5,824,834, and its aim is formulated as being that of minimizing disadvantages, i.e. outdated non-compliance with environmental protection regulations in the first process above and distinct yield losses in the second process above. It should be pointed out here that, according to Ullmanns Encyclopedia of Industrial Chemistry (5th Edition, Volume A1, pages 97-144) the amounts both of soot, coke and tar obtained and of higher alkynes and naphthalene rise in a greater-than-proportional manner in the case of modes of operation with oxygen ratios of $\lambda$<0.31, and can no longer be removed and retained to a sufficient degree by the separation concepts described in U.S. Pat. No. 5,824,834 in order to fulfill the applicable environmental protection regulations.

A further process for preparing acetylene and synthesis gas by partial oxidation of hydrocarbons with oxygen is described in EP-A 1 989 160. This is an extension of the process of U.S. Pat. No. 5,824,834, such that the remaining very fine solid components (soot, tar, coke) in the product gas are separated out by means of product gas compressors. In this case, the solids obtained in the already pre-purified product gas separate out in the cooling water injected directly into the product gas compressor and are discharged therefrom. However, a disadvantage is that the solids obtained are discharged here bound within the water. For commercial (dry) marketing of the solids, this entails an inconvenient and costly aftertreatment in the form of drying, which generally opposes commercially attractive marketing for reasons of cost.

Therefore, in the context of the European patent application with application number EP 12171956.1, essentially the combination of the three process concepts from Ullmanns Encyclopedia of Industrial Chemistry (5th Edition, Volume A1, pages 97-144), U.S. Pat. No. 5,824,834 and EP-A 1 989 160 is described. Additionally described is the separation of liquid and gaseous unwanted by-products (essentially higher alkynes and naphthalene) by means of partial vaporization (flash).

However, the above prior art does not give any pointer to the problem of the increased occurrence of soot, coke and tar, and how these can be separated out in dry form.

It was accordingly an object of the invention to provide a process for preparing acetylene and synthesis gas by partial oxidation of hydrocarbons which combines the advantages of the above processes, i.e. ensures both a high yield of acetylene product of value and compliance with the applicable environmental protection regulations through sufficient separation and retention of unwanted gaseous and/or liquid by-products, and which additionally enables sufficient dry removal and retention of solid unwanted by-products (tar, coke, soot).

The object is achieved by a continuous process for preparing acetylene and synthesis gas by partial oxidation of hydrocarbons with oxygen, in which a first input stream comprising one or more hydrocarbons and a second input stream comprising oxygen are separately heated in preheaters, mixed in a mixing unit in a ratio of the mass flow of the second input stream to the first input stream corresponding to an oxygen ratio of less than or equal to 0.31, the oxygen ratio being understood to mean the ratio of the amount of oxygen actually present in the second input stream to the amount of oxygen which is needed stoichiometrically and is required for the full combustion of the one or more hydrocarbons present in the first input stream, supplied via a burner block to a combustion chamber in which the partial oxidation of the hydrocarbons takes place, to obtain a first cracking gas stream $I_g$, wherein the first cracking gas stream $I_g$ is cooled in a prequench by injection of an aqueous quench medium to a temperature in the range from 100 to 1000° C. to obtain a second cracking gas stream $II_g$, in a solid-gas separation apparatus, 50 to 90% of the solids present in the second cracking gas stream $II_g$ are removed therefrom to obtain a solids stream $I_f$ and a third cracking gas stream $III_g$, the third cracking gas stream $III_g$ is cooled in a total quench by injection of water to 80 to 90° C. to obtain a fourth cracking gas stream $IV_g$ and a first process water stream $I_{liq}$, the fourth cracking gas stream $IV_g$ is subjected in one or more scrubbing apparatuses to a fine removal of solids to obtain one or more process water streams $II_{liq}$, $III_{liq}$ and a product gas stream $VI_g$, the process water streams $I_{liq}$, $II_{liq}$, $III_{liq}$ are combined to give a combined process water stream $IV_{liq}$, the combined process water stream $IV_{liq}$ is recycled partly as stream $V_{liq}$ into the total quench and the rest is subjected as stream $VI_{liq}$ to cleaning by partial vaporization in a one-stage flash vessel, stream $VI_{liq}$ being vaporized in a proportion of 0.01 to 10% by weight, based on the total weight thereof, to obtain a cleaned process water stream $VII_{liq}$ which is cooled by means of a re-cooling device, partly recycled as stream $VIII_{liq}$ into one or more of the one or more scrubbing apparatuses, and the rest is discharged as stream $IX_{liq}$, and supplied to the wastewater in need of treatment.

It has been found that the inventive process regime, through prequenching of the cracking gas stream from a process for continuously preparing acetylene and synthesis gas to a temperature in the range from 100 to 1000° C., avoids both unwanted condensation of water of reaction, quench water or tars prior to supply of the cracking gas stream obtained here to a downstream solid-gas separation apparatus, and thermal overloading of the solid-gas separation apparatus, and can additionally ensure stoppage of the synthesis reaction and hence an optimal acetylene yield.

By operating the solid-gas separation apparatus in accordance with the invention, in such a way that 50 to 90% of the solids from the cracking gas stream obtained in the prequench are removed therein, the amount of soot remaining in the cracking gas is so small that solely the discharge of a substream of the cleaned process water stream, especially in a flow rate corresponding to the water of reaction obtained from the partial oxidation of hydrocarbons with oxygen, into the wastewater in need of treatment can ensure steady-state, continuous operation of the plant.

It has been found that, surprisingly, by virtue of a further simple solid-gas separation apparatus connected downstream of the prequench, the total solids separation rate into the process water is sufficiently high, and hence obviates the need for an additional removal in a solid-gas separation apparatus, operated in a costly and inconvenient manner and with a high energy demand, in the form of an electrostatic filter. In addition, the proposed concept for solids separation makes the solids content in the process water obtained so low that continuous discharge of process water, especially in an amount corresponding to the water of reaction obtained in the partial oxidation of hydrocarbons with oxygen, into the wastewater in need of treatment enables continuous operation of the process without further, complex and water-intensive solid-liquid separation devices (soot channels).

The process according to the invention is independent of the specific form of the reactor system used, comprising mixing unit, burner block and quench unit.

The preferred reactor systems typically used are explained in detail hereinafter:

The starting materials, i.e. a first input stream comprising hydrocarbons, especially natural gas, and a second gas stream comprising oxygen, are heated separately, typically up to 600° C. In a mixing unit, the reactants are mixed vigorously and, after flowing through a burner block, are reacted exothermically in a combustion chamber. The burner block typically consists of a multitude of parallel channels in which the flow rate of the ignitable oxygen/hydrocarbon mixture is higher than the flame speed, in order to prevent the flame from striking through into the mixing unit. The metallic burner block is cooled in order to withstand the thermal stresses. According to the residence time in the mixing unit, there is the risk of pre- and re-ignition due to the limited thermal stability of the mixtures. For this purpose, the term "ignition delay time" or "induction time" is used as the period of time within which an ignitable mixture does not undergo any significant intrinsic thermal change. The induction time depends on the nature of the hydrocarbons used, the mixing state, pressure and temperature. It determines the maximum residence time of the reactants in the mixing unit. Reactants such as hydrogen, liquefied gas or light gasoline, the use of which is particularly desirable due to yield and/or capacity increases in the synthesis process, feature comparatively high reactivity and hence a short induction time.

The acetylene burners being used on the current production scale are notable for the cylindrical geometry of the combustion chamber. The burner block has passage bores preferably in a hexagonal arrangement. In one embodiment, for example, 127 bores of internal diameter 27 mm are arranged hexagonally on a circular base cross section with a diameter of approx. 500 mm. In general, the channel diameters used are about 19 to 27 mm in diameter. The downstream combustion chamber in which the flame of the partial oxidation reaction, which forms acetylene and synthesis gas, is stabilized is typically likewise of cylindrical cross section, is water-cooled and corresponds in terms of appearance to that of a short tube, for example of diameter 180 to 533 mm and length 380 to 450 mm. At the level of the burner block, what is called auxiliary oxygen is supplied to the combustion chamber both in the axial and in the radial direction. This ensures flame stabilization and hence a defined separation of the flame roots and hence of the commencement of reaction from the stopping of the reaction by the quench unit.

The overall burner composed of burner block and combustion chamber is preferably suspended from the top by means of a flange into a quench vessel of greater cross section. At the level of the exit plane from the combustion chamber, on the outer circumference thereof, are installed quench nozzles on one or more quench distributor rings, which atomize the quench medium with or without the aid of an atomization medium and inject it virtually at right angles to the main flow direction of the reaction gases leaving the combustion chamber. This direct quench has the task of cooling the reaction mixture extremely rapidly, such that further reactions, i.e. especially the degradation of acetylene formed, are frozen. The range and distribution of the quench jets is ideally such that a very homogeneous temperature distribution is achieved within a very short time.

The present industrial process forms, as well as acetylene, essentially hydrogen, carbon monoxide and soot. The soot particles formed in the flame front can adhere as seeds to the combustion chamber side walls, which then results, under suitable physicochemical conditions, in growth, deposition and caking of coke layers.

These deposits are removed by mechanical cleaning periodically in the region of the combustion chamber walls by means of a poker unit, as described, for example, in Ullmanns Encyclopedia of Industrial Chemistry 5th Edition, Volume A1, pages 97-144 or in U.S. Pat. No. 5,824,834.

For a further preferred embodiment, the reactor system has a flushed reactor side wall as described in WO-A 2012/062784, or a flushed reactor end face as described in WO-A 2012/062584. In these embodiments, the above-described mechanical poking can be dispensed with, and this avoids entrainment of large-scale solid portions downstream and hinders the continuation of the process there—for example through blockage of separation and/or heat exchanger apparatuses.

In an advantageous embodiment, 60 to 80% of the solids present in the second cracking gas stream $II_g$ are separated therefrom in the solid-gas separation apparatus.

The solids stream $I_f$ separated out in the solid-gas separation apparatus comprises predominantly tars, soots and cokes.

The solid-gas separation apparatus is advantageously a cyclone separator.

Advantageously, the first cracking gas stream $I_g$ is cooled in the prequench to a temperature in the range from 200 to 650° C.

Further advantageously, the first cracking gas stream $I_g$ is cooled in the prequench to a temperature in the range from 250 to 400° C.

The prequench is advantageously a water quench.

A particularly advantageous embodiment in terms of energy is one in which the prequench comprises a heat exchanger for extracting heat of reaction in the form of high-pressure steam.

Preferably, the first scrubbing apparatus used is a Venturi scrubber and the second scrubbing apparatus a quench column.

The cleaned process water substream $VIII_{liq}$ is preferably recycled into the second scrubbing apparatus.

In a preferred embodiment, the re-cooling device is a closed re-cooling device.

In a further preferred embodiment, the re-cooling device is an open cooling tower. In this process variant, the entire cleaned process water stream is preferably recycled into the process.

The invention is illustrated hereinafter by a drawing and by working examples.

FIG. 1 shows the schematic diagram of a preferred plant design of the invention.

The preferred plant shown in FIG. 1 for performance of the process according to the invention is supplied with a first input stream 1 comprising one or more hydrocarbons, and a second oxygen-comprising input stream 2, these being preheated separately by means of preheaters V1 and V2, mixed in a mixing unit M, supplied via a burner block BR to a combustion chamber FR to obtain a first cracking gas stream $I_g$, which is supplied to a prequench H and quenched therein by injecting an aqueous quench medium, not shown in the FIGURE to 100 to 1000° C. In the preferred embodiment shown in the FIGURE, this extracts heat of reaction from the prequench H in the form of high-pressure stream. The second cracking gas stream $II_g$ which leaves the prequench H is supplied to a solid-gas separation apparatus A which is designed such that 50 to 90% of the solids present in the second cracking gas stream $II_g$ especially soots, tars and cokes, are removed therein to obtain a solids stream $I_f$, which is drawn off, and a third cracking gas stream $III_g$, which is supplied to a total quench B and is cooled therein by direct water injection to 80 to 90° C. to obtain a fourth cracking gas stream $IV_g$ and a first process water stream $I_{liq}$. In the preferred embodiment shown in the FIGURE, the fourth cracking gas stream $IV_g$ is supplied to a first scrubbing apparatus C, and separated therein into a fifth cracking gas stream $V_g$ and a second process water stream $II_{liq}$ The cracking gas stream $V_g$ is supplied to a second scrubbing apparatus D and separated therein into a product gas stream $VI_g$ and a further process water stream $III_{liq}$ The process water streams $I_{liq}$, $II_{liq}$, $III_{liq}$ are combined to give a combined process water stream $IV_{liq}$, which is recycled partly as process water stream $V_{liq}$ into the total quench B and the rest is supplied as process water stream $VI_{liq}$ to a one-stage flash vessel E, in which partial vaporization is effected to obtain a cleaned process water stream $VII_{liq}$, which is cooled by means of a re-cooling device F and partly discharged via a valve G as process water stream $IX_{liq}$, and the rest, as process water stream $VIII_{liq}$, in two substreams in the preferred embodiment shown in the FIGURE, is recycled into the second scrubbing apparatus D. The mass flow of the process water stream $IX_{liq}$ is preferably adjusted such that the amount of water which is obtained in the reaction, i.e. the partial oxidation of hydrocarbons with oxygen, is discharged.

The product gas stream $VI_g$, as a product-of-value stream comprising essentially acetylene, carbon monoxide and hydrogen, is supplied as a crude product gas to a fine purification and product gas separation, and fed into the corresponding chemical value-addition chain.

WORKING EXAMPLES

Comparative Example

Without cleaning the process water to remove the gaseous and liquid unwanted by-products, in a plant corresponding to the schematic diagram in Ullmanns Encyclopedia of Industrial Chemistry 5th Edition, Volume A1, pages 97-144, the following emissions are obtained in specific terms from the open soot channels and the air output of the cooling tower for 1 t of acetylene in the case of performance of the partial oxidation with an oxygen ratio of 0.29:

|  | Soot channels [kg] | Cooling tower [kg] | Total [kg] |
| --- | --- | --- | --- |
| CO | 0.303 | 0.363 | 0.667 |
| methane | 5.67E−02 | 8.46E−02 | 0.141 |
| ethane | 7.63E−03 | 1.21E−02 | 0.020 |
| ethylene | 6.80E−03 | 2.88E−02 | 0.036 |
| acetylene | 1.57E−01 | 6.05E+00 | 6.203 |
| propene | 5.16E−04 | 1.88E−03 | 0.002 |
| propadiene | 9.83E−04 | 3.58E−03 | 0.005 |
| propyne | 2.29E−03 | 1.01E−01 | 0.103 |
| butenyne | 1.65E−03 | 4.58E−02 | 0.047 |
| butadiyne | 7.39E−03 | 8.91E−01 | 0.898 |
| benzene | 2.29E−03 | 1.60E−01 | 0.162 |
| naphthalene | 5.14E−04 | 1.40E−02 | 0.014 |

In addition, 57 kg/t of acetylene are separated out of the process water in wet form by means of soot channels and electrostatic filters.

Working Example According to the Invention

In the performance of a partial oxidation of natural gas with oxygen, at a ratio of the mass flow of the natural gas stream to the oxygen-comprising gas stream corresponding to an oxygen ratio of 0.29 and in accordance with achievement of a high yield, of greater than 8%, of acetylene product of value, the prequench H was considered to be a hot cyclone separator, the first scrubbing apparatus C to be a Venturi scrubber and the second scrubbing apparatus D to be a cooling column.

In the process, 65.57 kg of soot are formed per tonne of acetylene.

In the case of a deposition level of 80% of the soot in the prequench H, i.e. a dry deposition, a residual content of 13.11 kg of soot per tonne of acetylene remains in the cracking gas downstream of the prequench H.

In the case of a deposition level of 90% by means of wet fine deposition in the Venturi scrubber C, 1.31 kg of soot per tonne of acetylene remain in the cracking gas stream $V_g$, which leaves the Venturi scrubber C. In the case of further wet fine deposition in the cooling column D, with a deposition level of 30%, a residual content of 0.92 kg of soot per tonne of acetylene remains in the cracking gas stream $VI_g$, this being tolerable.

In the above process, 80% of the total solids content is thus separated out of the cracking gas in dry form using a hot gas cyclone as the prequench H, such that marketing thereof is possible without further energy-intensive drying steps. In comparison to this, only the remaining 20% of the solids content are separated out in wet form by means of simple, high-efficiency separation apparatuses, i.e. Venturi scrubber and cooling column. Soot channels and electrostatic filters are no longer required as a result. Solids separation by the process according to the invention by means of a prequench results in such a low solids content in the cleaned process water (13.11 kg of soot per tonne of acetylene), that continuous discharge of a substream of the cleaned process water, preferably according to the water of reaction obtained in the partial oxidation, enables continuous operation of the process without further, complex and water-intensive solid-liquid separation devices, more particularly soot channels.

A similarly low proportion of solids in the process water has to date been possible according to the prior art, for example in accordance with U.S. Pat. No. 5,824,834, only in the case of a lean mode of operation, i.e. with an oxygen ratio of 0.32 and correspondingly with acceptance of a lower yield of acetylene of only 6%.

Table 1 below reports the depletion by the cleaning step of the removal of unwanted liquid and gaseous by-products in a cooling tower in percent.

TABLE 1

|  | Cooling tower kg/t of acetylene | Depletion % |
| --- | --- | --- |
| CO | 1.20E−04 | 99.9820 |
| methane | 3.53E−05 | 99.9750 |
| ethane | 5.39E−06 | 99.9726 |
| ethylene | 3.55E−05 | 99.9002 |
| acetylene | 6.67E−02 | 98.9253 |
| propene | 1.99E−06 | 99.9172 |
| propadiene | 3.78E−06 | 99.9172 |
| propyne | 1.37E−03 | 98.6727 |
| butenyne | 3.90E−04 | 99.1785 |
| butadiyne | 3.62E−02 | 95.9707 |
| benzene | 3.36E−03 | 97.9296 |
| naphthalene | 1.01E−04 | 99.3007 |

Owing to the high depletion rate, the cooling tower can be replaced by a closed heat exchanger without resulting in intolerable accumulations of polymerizable components, especially of higher acetylenes, in the process.

|  | Secondary components in the process water | |
| --- | --- | --- |
|  | Closed water quench without flash [ppm by weight] | Closed water quench with flash [ppm by weight] |
| CO | 1.846 | 0.001 |
| methane | 0.430 | 0.000 |
| ethane | 0.061 | 0.000 |
| ethylene | 0.146 | 0.000 |
| acetylene | 30.537 | 0.333 |
| propene | 0.010 | 0.000 |
| propadiene | 0.018 | 0.000 |
| propyne | 0.514 | 0.007 |
| butenyne | 0.233 | 0.002 |
| butadiyne | 4.606 | 0.182 |
| benzene | 0.018 | 0.017 |
| naphthalene | 0.071 | 0.001 |

The invention claimed is:

1. A continuous process for preparing acetylene and synthesis gas by partial oxidation of hydrocarbons with oxygen, comprising:
separately heating in preheaters a first input stream comprising one or more hydrocarbons and a second input stream comprising oxygen, mixing in a mixing unit the first and second input streams in a ratio of mass flow of the second to first input stream corresponding to an oxygen ratio of less than or equal to 0.31, wherein the oxygen ratio is the amount of oxygen present in the second input stream to the amount of oxygen which is needed stoichiometrically for full combustion of one or more hydrocarbons in the first input stream, supplying said mixture of the first and second streams via a burner block to a combustion chamber configured for partial oxidation of the one or more hydrocarbons, thus obtaining a first cracking gas stream $I_g$;

cooling in a prequench said first cracking gas stream $I_g$ by injecting an aqueous quench medium to a temperature of 100 to 1,000° C., thus obtaining a second cracking gas stream $II_g$;

removing in a solid-gas separation apparatus 50 to 90% of the solids present in the second cracking gas stream $II_g$ thus obtaining a solids stream $I_f$ and a third cracking gas stream $III_g$, cooling in a total quench the third cracking gas stream $III_g$ by injecting water to a temperature of 80 to 90° C. to obtain a fourth cracking gas stream $IV_g$ and a first process water stream $I_{liq}$, scrubbing in one or more scrubbing apparatuses the fourth cracking gas stream $IV_g$ to remove solids, thus obtaining process water streams $II_{liq}$, or $II_{liq}$ and $III_{liq}$, and a product gas stream $VI_g$, combining process water streams $I_{liq}$, $II_{liq}$, $III_{liq}$ thus providing a combined process water stream $IV_{liq}$, recycling the combined process water stream $IV_{liq}$ partly as stream $V_{liq}$ into the total quench and partly as stream $VI_{liq}$ to cleaning by partial vaporization in a one-stage flash vessel that being vaporizes stream $VI_{liq}$ in a proportion of 0.01 to 10% by weight, based on the total weight thereof, to obtain a cleaned process water stream $VII_{liq}$, cooling with a re-cooling device cleaned process water stream $VII_{liq}$ and partly recycling it as stream $VIII_{liq}$ into one or more of the one or more scrubbing apparatuses, and partly discharging the rest as stream $IX_{liq}$.

2. The continuous process according to claim 1, wherein stream $IX_{liq}$ is discharged at a flow rate corresponding to the water of reaction obtained in the partial oxidation of the hydrocarbons with oxygen.

3. The continuous process according to claim 1, wherein 60 to 80% of the solids present in the second cracking gas stream $II_g$ is separated therefrom in the solid-gas separation apparatus.

4. The continuous process according to claim 1, wherein the solids stream $I_f$ comprises tars, soots and cokes.

5. The continuous process according to claim 1, wherein the solid-gas separation apparatus is a cyclone separator.

6. The continuous process according to claim 1, wherein the first cracking gas stream $I_g$ is cooled in the prequench to a temperature in the range from 200 to 650° C.

7. The continuous process according to claim 6, wherein the first cracking gas stream $I_g$ is cooled in the prequench to a temperature in the range from 250 to 400° C.

8. The continuous process according to claim 1, wherein the prequench is a water quench.

9. The continuous process according to claim 8, wherein the prequench comprises a heat exchanger for extracting heat of reaction in the form of high-pressure steam.

10. The continuous process according to claim 1, wherein the one or more scrubbing apparatuses comprise a first scrubbing apparatus used is a Venturi scrubber and the second scrubbing apparatus a quench column.

11. The continuous process according to claim 1, wherein the one or more scrubbing apparatuses comprise a first and second scrubbing apparatus, and wherein the cleaned process water substream $VIII_{liq}$ is supplied to the second scrubbing apparatus.

12. The continuous process according to claim 1, wherein the re-cooling device is a closed re-cooling device.

13. The continuous process according to claim 1, wherein the re-cooling device is an open cooling tower.

\* \* \* \* \*